(12) United States Patent
Gary et al.

(10) Patent No.: US 7,153,985 B1
(45) Date of Patent: Dec. 26, 2006

(54) ETHYLENE OXIDE PRODUCTION

(75) Inventors: Melvin R. Gary, Pasadena, TX (US);
Jimmy W. White, Pasadena, TX (US);
Michael G. Lenway, Kountze, TX (US)

(73) Assignee: Equistar Chemicals, LP, Houston, TX (US), part interest ( * ) Notice: Subject to any disclaimer, the term of this patent is extended or adjusted under 35 U.S.C. 154(b) by 0 days.

(21) Appl. No.: 11/333,077

(22) Filed: Jan. 17, 2006

(51) Int. Cl.
*C07D 301/08* (2006.01)

(52) U.S. Cl. ........................ 549/523; 549/534; 549/538

(58) Field of Classification Search ............... 549/534, 549/538, 523
See application file for complete search history.

(56) References Cited

U.S. PATENT DOCUMENTS

| 4,769,047 | A | * | 9/1988 | Dye | 95/97 |
| 6,727,389 | B1 | | 4/2004 | Viswanathan | 564/477 |

* cited by examiner

*Primary Examiner*—Bernard Dentz
(74) *Attorney, Agent, or Firm*—Roderick W. MacDonald

(57) ABSTRACT

A process for the formation of ethylene oxide wherein the presence of at least one hydrocarbon having four carbon atoms per molecule in the recycle loop gas of the process is used as an indicator of impending post-ignition conditions.

7 Claims, 2 Drawing Sheets

ETHYLENE OXIDE PRODUCTION

BACKGROUND OF THE INVENTION

This invention relates to the production of ethylene oxide (EO). More particularly, it relates to the detection or otherwise sensing of impending flame formation conditions at an EO reactor (reactor).

DESCRIPTION OF THE PRIOR ART

In a conventional ethylene oxide production plant (plant), ethylene and oxygen are reacted at an elevated temperature of from about 500 degrees Fahrenheit (F) to about 550 F under slight pressure in the presence of a catalyst to form EO. The reaction is fast, on the order of about one second, and high yielding, approaching 90%. The EO reaction product is normally gaseous and contains newly formed EO, unreacted ethylene, and by-products, mainly carbon dioxide ($CO_2$).

The EO is separated from the ethylene and by-products in a water-wash column (EO absorber) in the manner of a solvent recovery process. The vast majority of the EO is absorbed by the water, and the ethylene and by-products are not. The resulting EO/water solution is then steam stripped and purified by thermal distillation. The ethylene and by-products are split with the ethylene being recycled by way of the recycle gas loop to the reactor, and the by-products plus very minor amounts of ethylene being separately recovered for other processing and disposition. This process yields about 1.4 pounds of EO per pound of ethylene feed at high yields. Yields can, however, vary widely from plant to plant worldwide. For a full and complete description of an EO production plant see U.S. Pat. No. 6,727,389.

EO as a liquid boils at about 56 F to form a colorless gas at room temperature. EO is traded commercially as a high purity, e.g., 99.7%, technical grade chemical. Because of its volatility under normal conditions, care must be given in the storage and transportation of EO to keep it out of the ambient atmosphere. EO is an intermediary chemical useful for making a number of derivatives of commercial value.

The goal in an EO production plant is an essentially constant EO production rate even as the catalyst in the reactor ages and its selectivity for the formation of EO decreases. To keep EO production at a high level under such circumstances the flow of ethylene and oxygen to the reactor is increased.

The EO formation reaction is exothermic and is run near the flammable point for the mixture of materials present at the reactor because ethylene selectivity and catalyst activity increases with temperature. This is so at both the inlet and outlet of the reactor. In normal operation, the oxygen content of this mixture of materials is kept below that which will cause flame formation in this mixture.

However, there are times when the conditions of temperature, pressure, and/or composition of this mixture of materials favor the formation of a flame front at a reactor. Such a condition is termed "post-ignition" in a conventional plant.

There can be many causes for post-ignition, some of which are not readily obvious. For example, the presence of catalyst dust can alter a composition's disposition toward flammability. Since there is nothing in the reactor to remove heat, temperatures can rise to an extent that thermal cracking of ethylene can occur with the consequent formation of other hydrocarbon molecules. These hydrocarbon molecules can contribute to a flammability propensity, and when they combust at essentially the same time, detonation can occur with the result of the formation of a flame front.

A flame front at the outlet of a reactor is not desirable. However, since there is less oxygen present at this location of the reactor, a post-ignition event will usually not damage equipment, e.g., crack piping. Also, the flame front is normally extinguished when it reaches the first heat exchanger immediately downstream of the reactor. A post-ignition event at the inlet of a reactor is more dangerous, and is more likely to damage equipment because there is more oxygen present at this location.

Heretofore, the presence of propane or propylene has been used as an indicator of an impending post-ignition event, but these materials appear earlier in the process of building up to flammability conditions, and can cause premature remedial action to be taken.

Accordingly, it is desirable to have a post-ignition indicator that is operative later in the build-up process, and closer to the point of actual post-ignition.

SUMMARY OF THE INVENTION

It has been found that the presence of hydrocarbons having four carbon atoms per molecule ($C_4$'s) are an effective impending post-ignition condition indicator that manifests itself closer to the post-ignition point at an EO reactor, but still leaves sufficient time for an operator to take remedial action.

The $C_4$ markers (indicators) of this invention are more stable materials, consistently appear after propane and propylene appear, and appear much closer to the point of post-ignition.

DETAILED DESCRIPTION OF THE INVENTION

Figure 1:
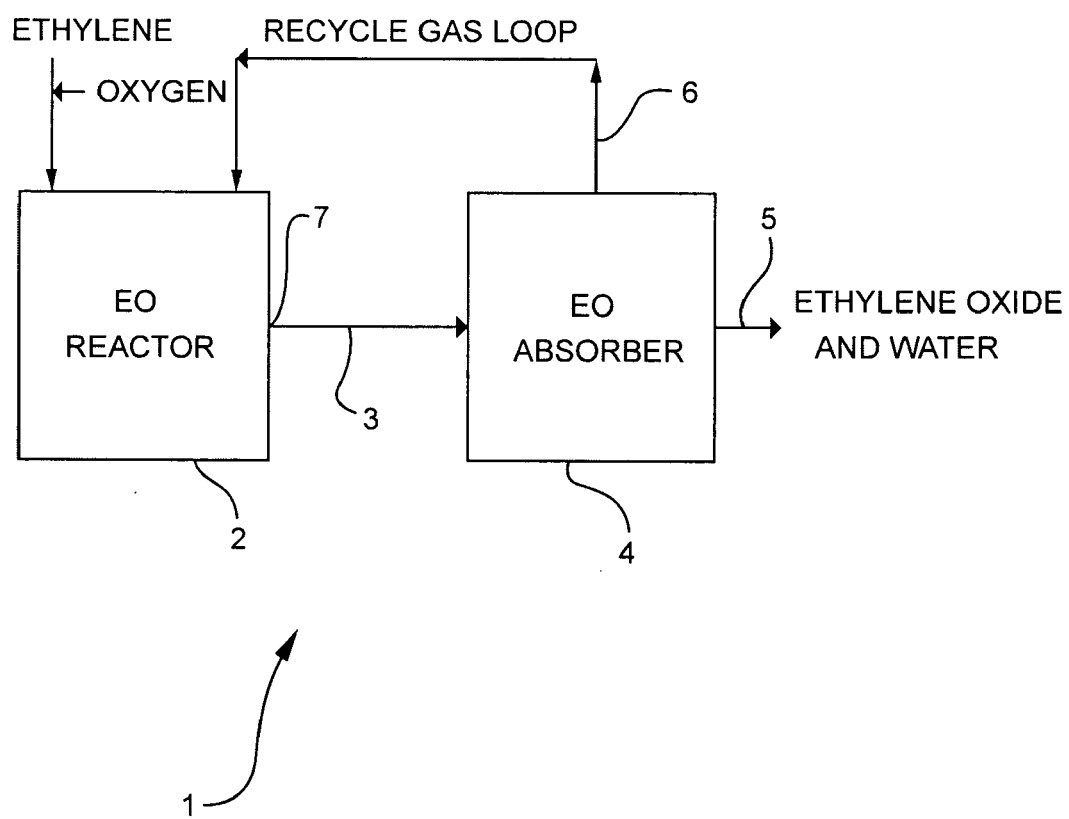
FIG. 1 shows a block diagram of the interrelationship of an EO reactor with an EO absorber in a conventional plant, including the recycle gas loop between these two units.

FIG. 1 shows the first two units of a typical EO production plant. The first unit is reactor 2. Ethylene feed and a separate oxygen feed are mixed and then reacted in unit 2 to form EO with the consequent formation of by-product as aforesaid. Unit 2 forms a first, normally gaseous, reaction product stream 3 that contains a major amount of newly formed EO, a substantial amount of free $CO_2$ and a minor amount of unreacted ethylene. Stream 3 is removed from outlet 7 of reactor 2.

The second unit in FIG. 1 is EO absorber 4 which is a water wash scrubber that operates in known manner as a solvent extractor by absorbing (dissolving) EO out of stream 3 to form a principally EO/water stream 5. Stream 5 is normally at a temperature of from about 75 to about 105 F under a pressure of about 220 psig, and is primarily a water stream that can contain from about 3 to about 5 weight percent (wt. %), based on the total weight of stream 5, EO dissolved therein. Stream 5 is then further processed in a manner that is not shown here for sake of brevity, but is shown in its entirety in U.S. Pat. No. 6,727,389. Such further processing recovers, as products of the plant, purified EO and/or derivatives thereof such as one or more glycols. In some processes the EO is not purified, but rather is converted into ethylene glycol.

Absorber 4 also produces a normally gaseous by-product stream 6 that is part of the plant recycle gas loop. The recycle gas in stream 6 can contain from about 55 to about 97 wt. % methane, from about 20 to about 40 wt. % unreacted ethylene, from about 3 to about 5 wt. % $CO_2$, and a trace of EO, all wt. % being based on the total weight of stream 6. Ideally, stream 6 is essentially free of $C_4$'s. Stream 6 is recycled to reactor 2 by way of the plant recycle gas loop for reuse of the unreacted ethylene as feed material in reactor 2, and in so doing, all or a substantial part of stream 6 can be processed for the removal of $CO_2$ there from.

Figure 2:
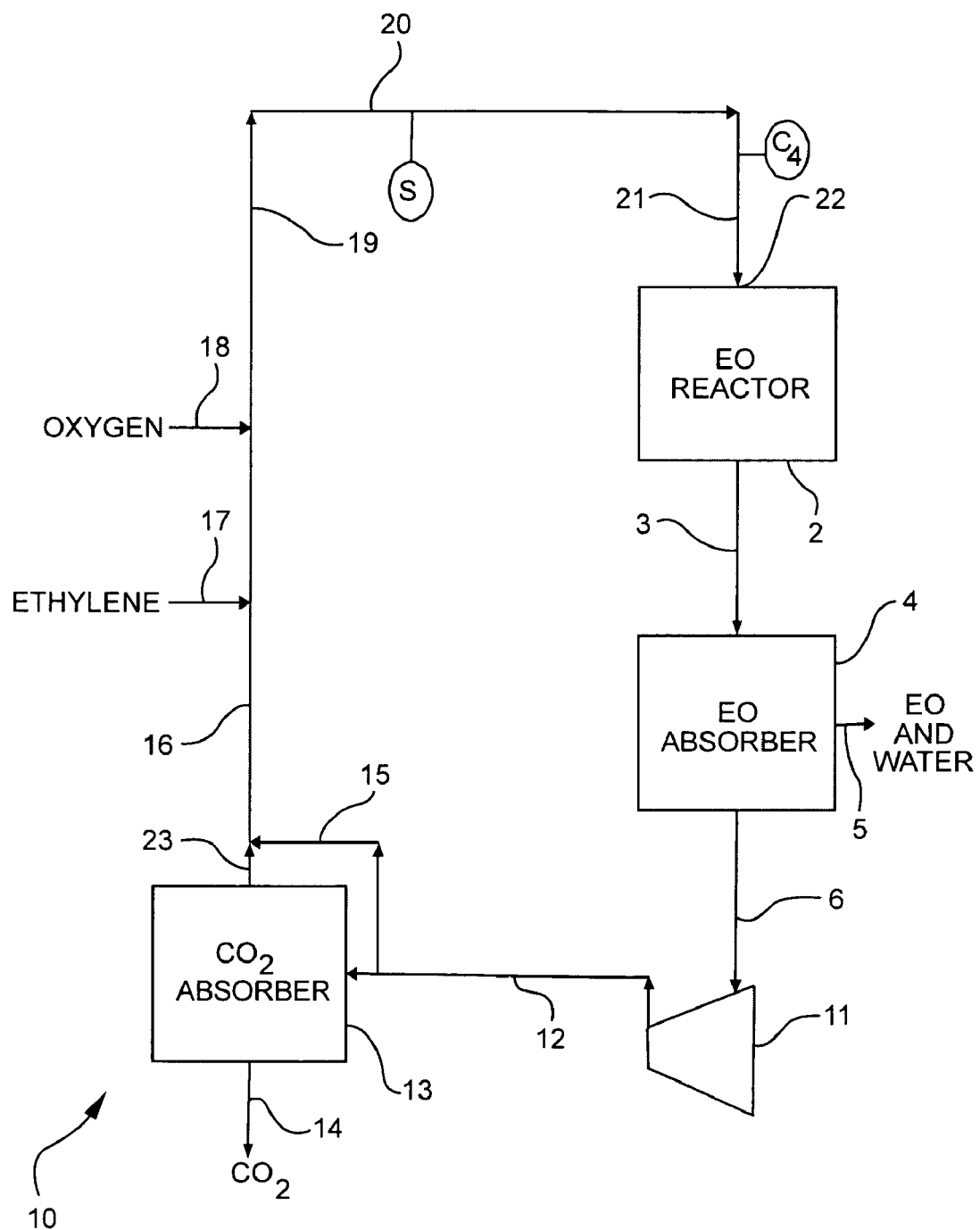
FIG. 2 shows the recycle gas loop of FIG. 1 in greater detail, and includes one embodiment within this invention.

FIG. 2 shows in greater detail a typical recycle gas loop 10 wherein recycle stream 6 from absorber 4 is first passed to a compression unit 11. The compressed gaseous product of unit 11 is removed by way of line 12. All or any part of stream 12 can be passed into $CO_2$ absorber 13 for removal of an essentially totally $CO_2$ stream 14. Alternatively, all or any part of stream 12 can by-pass unit 13 by way of line 15 and pass into line 16. Stream 16, which is essentially of the composition of stream 6, except it can contain a lesser amount of $CO_2$, has additional ethylene feed 17 added thereto, after which it passes into an oxygen mix nozzle (not shown) by which additional oxygen 18 is added to the mixture of materials. This feed mixture is then passed by way of lines 19, 20, and 21 to the inlet 22 of reactor 2 for reaction of ethylene and oxygen therein as aforesaid.

Lines 19 through 22 can typically carry an array of individual sensors such as a high pressure sensor, high temperature sensor, high oxygen sensor, and high ethylene sensor. These individual sensors are shown collectively as sensor S in FIG. 2.

Pursuant to this invention one of these lines, preferably line 21, carries, in addition to sensors S, a sensor $C_4$ which sensor is used to detect the $C_4$ compound content in that stream. This detection step will, by way of this invention, indicate incipient post-ignition developments at or near reactor inlet 22.

The $C_4$ indicators of this invention can be at least one of n-butane, iso-butane, iso-butylene, butenes, and butynes. A presently preferred marker is n-butane which, for sake of clarity only and not by way of limitation, will be used in the description hereinafter.

The sensing equipment for sensor $C_4$, and its operation are well known in the art. An example of such equipment is a standard gas chromatograph which is well known in the art and does not require further description to inform the art. As mentioned earlier, stream 21 is ideally devoid of any n-butane. However, there is often a very low background noise for $C_4$ compounds, typically 0.04 parts per million (ppm). Sensor $C_4$ is set at a level above this $C_4$ background noise level for warning purposes. Sensor $C_4$ can also be set to trigger at least one alarm or other warning device once a predetermined level of n-butane is detected in stream 21. For example, a first alarm or other mechanism can be triggered at a first lower n-butane level to be a warning signal for the operator to watch the n-butane content of the recycle stream more closely, but not necessarily to take any remedial action. A second alarm or other warning device can be triggered at a predetermined higher n-butane level that has been previously determined to indicate that immediate remedial action must promptly be taken by the operator in order to avoid post-ignition at or near intake 22 in the near future.

Once the remedial action alarm is sounded, the operator then knows to take such action immediately, e.g., by reducing the oxygen 18 feed rate. Once the n-butane content of stream 21, as detected by sensor $C_4$, has decreased to a predetermined level that is below the level set for the first or warning alarm, for example, the feed rate for oxygen 18 can be slowly increased until it is back to its normal feed rate level for the reaction conditions then being present in the reactor.

EXAMPLE

An EO plant as described here in above provides a recycle gas loop stream 6 having a volume of about 2,000,000 pounds per hour (pph) and containing about 50 wt. % methane, about 36 wt. % unreacted ethylene, about 2.5 wt. % $CO_2$, no more than about 0.04 ppm n-butane, and about 100 ppm EO, all based on the total weight of stream 6. About 1,000 kpph of recycle loop gas 6 is split off from the recycle loop and passed to $CO_2$ absorber 13. Stream 23 from absorber 13 returns about 960,000 pph of recycle gas to the loop. Stream 23 has a composition of about 36 wt. % ethylene, about 50 wt. % methane, up to about 1 wt. % $CO_2$, about 10 wt. % elemental oxygen and argon, and a trace of EO, all wt. % based on the total weight of stream 23. Streams 23 and 15 are combined into stream 16, and this stream has added thereto ethylene feed 17 and oxygen feed 18 in amounts sufficient to form a feed stream 22 for reactor 2 having a composition of about 40 wt. % ethylene, about 8 wt. % oxygen, about 50 wt. % methane, about 1.3 wt. % $CO_2$, a trace of EO, and no more than about 0.04 ppm n-butane.

The butane content of this stream is monitored for its n-butane content on a continuous manner using a standard gas chromatograph.

When the n-butane content of this stream reaches a level of 0.10 ppm, a warning alarm is triggered to focus the operator on this process parameter.

When the n-butane content of this stream reaches a level of 0.20 ppm second alarm is triggered that signals the operator to take remedial action promptly in order to avoid a post-ignition event.

The operator promptly reduces the flow of oxygen 18 into line 19 in order to alter the conditions that were trending toward the formation of a flame front.

We claim:

1. In a method for forming ethylene oxide in a reactor having an inlet and outlet, wherein ethylene and oxygen are fed to said inlet and an ethylene oxide containing stream is recovered from said outlet, said ethylene oxide containing stream having EO removed there from to leave a recycle stream that is returned to said inlet, the improvement comprising determining the content of said recycle stream as to at least one hydrocarbon having four carbon atoms per molecule, and using an increase of said hydrocarbon content in said recycle stream as an indicator of impending post-ignition conditions.

2. The method of claim 1 wherein said at least one hydrocarbon is at least one of n-butane, iso-butane, iso-butylene, at least one butene, and at least one butyne.

3. The method of claim 1 wherein said at least one hydrocarbon is n-butane.

4. The method of claim 3 wherein a close watch of said butane content is made when said n-butane content in said recycle stream reaches about 0.10 ppm.

5. The method of claim 3 wherein post-ignition avoidance remedial action is taken when said n-butane content in said recycle stream reaches about 0.20 ppm.

6. The method of claim 5 wherein said remedial action is at least a decrease in the amount of said oxygen fed to said inlet.

7. The method of claim 1 wherein said hydrocarbon content determination is made at least one of said inlet and outlet.

* * * * *